(12) United States Patent
Yamanishi et al.

(10) Patent No.: US 10,612,155 B2
(45) Date of Patent: Apr. 7, 2020

(54) METHOD FOR CRYSTALLIZING PROTEIN

(71) Applicant: JAPAN SCIENCE AND TECHNOLOGY AGENCY, Kawaguchi-shi, Saitama (JP)

(72) Inventors: Yoko Yamanishi, Tokyo (JP); Fumihito Arai, Nagoya (JP); Hiroki Kuriki, Nagoya (JP)

(73) Assignee: JAPAN SCIENCE AND TECHNOLOGY AGENCY, Kawaguchi-Shi (JP)

( * ) Notice: Subject to any disclaimer, the term of this patent is extended or adjusted under 35 U.S.C. 154(b) by 1045 days.

(21) Appl. No.: 14/914,755

(22) PCT Filed: Aug. 27, 2014

(86) PCT No.: PCT/JP2014/072387
§ 371 (c)(1),
(2) Date: Feb. 26, 2016

(87) PCT Pub. No.: WO2015/030038
PCT Pub. Date: Mar. 5, 2015

(65) Prior Publication Data
US 2016/0208405 A1 Jul. 21, 2016

(30) Foreign Application Priority Data

Aug. 30, 2013 (JP) ................. 2013-179848

(51) Int. Cl.
*C30B 7/12* (2006.01)
*C07K 1/30* (2006.01)
(Continued)

(52) U.S. Cl.
CPC ................ *C30B 7/12* (2013.01); *C07K 1/306* (2013.01); *C07K 14/80* (2013.01); *C12N 9/0016* (2013.01);
(Continued)

(58) Field of Classification Search
CPC ........... C07K 1/306; C30B 7/12; C30B 29/58; C30B 30/02; C30B 33/04
See application file for complete search history.

(56) References Cited

U.S. PATENT DOCUMENTS 6,210,404 B1  4/2001  Shadduck
6,846,306 B1  1/2005  Haas et al.
(Continued)

FOREIGN PATENT DOCUMENTS

JP  2004-277255 A  10/2004
JP  2006-263419 A  10/2006
(Continued)

OTHER PUBLICATIONS

Y. Yamanishi et al., "Electric knife for cell surgery: Local ablation by micro-plasma discharge," 2012 IEEE 25th International Conference on Micro Electro Mechanical Systems (MEMS), pp. 945-948 (Jan. 29-Feb. 2, 2012).
(Continued)

*Primary Examiner* — Arun S Phasge (57) ABSTRACT

Provided are a protein crystal device and method for crystallizing protein capable of generating protein crystal without imparting a heat effect, a protein crystal-cutting device and method for cutting protein crystal capable of cutting protein crystal without imparting a heat effect on protein crystal, and bubble-jetting member and protein-adsorbing-bubble-jetting member used in said device. A bubble-jetting member is used in a protein crystal device to jet bubbles into a protein solution to thereby allow protein crystals to be obtained, the bubble-jetting member comprising: a core formed of a conductive material; a shell part formed of an insulating material, including an extended section extending from the tip of the core, and in which at least a portion closely adheres to the core to cover the core; and a gap
(Continued)

having a bubble-jetting port, the gap being formed between the extended section and the tip of the core.

5 Claims, 7 Drawing Sheets (51) Int. Cl.
*C30B 29/58* (2006.01)
*C07K 14/80* (2006.01)
*C12N 9/06* (2006.01)
*C12N 9/36* (2006.01)
*C30B 30/02* (2006.01)
*C30B 33/04* (2006.01)

(52) U.S. Cl.
CPC .... *C12N 9/2462* (2013.01); *C12Y 104/01014* (2013.01); *C30B 29/58* (2013.01); *C30B 30/02* (2013.01); *C30B 33/04* (2013.01)

(56) References Cited

U.S. PATENT DOCUMENTS

| | | | |
|---|---|---|---|
| 2002/0183741 A1 | 12/2002 | Carmel | |
| 2003/0125727 A1 | 7/2003 | Truckai | |
| 2005/0241568 A1 | 11/2005 | Sasaki et al. | |
| 2007/0029292 A1 | 2/2007 | Suslov | |
| 2010/0317118 A1 | 12/2010 | Masujima et al. | |
| 2011/0042215 A1* | 2/2011 | Hou | B01D 9/00 204/547 |

FOREIGN PATENT DOCUMENTS

| | | |
|---|---|---|
| JP | 2009-500799 A | 1/2009 |
| WO | 98/12974 A1 | 4/1998 |
| WO | 00/71038 A1 | 11/2000 |
| WO | 2004/018744 A1 | 3/2004 |
| WO | 2009/063776 A1 | 5/2009 |
| WO | 2013/129657 A1 | 9/2013 |

OTHER PUBLICATIONS

European Patent Office, "Extended European Search Report," issued in European Patent Application No. 14 839 877.9, which is a European counterpart of U.S. Appl. No. 14/914,755, dated Jan. 30, 2017, 11 pages.
Y. Yamanishi et al., "Transportation of micro-plasma bubble in micro-fluidic chip under atmospheric pressure", IC-Plants 2013, The 6th International Conference on PLAsma-Nano Technology & Science, O-03 (Feb. 2-3, 2013), Gero Synergy Center, Gero City, Gifu, Japan.
Takahiro Kaji et al., "Nondestructive micropatterning of living animal cells using focused femtosecond laser-induced impulsive force", Applied Physics Letters, vol. 91, 023904 (2007), AIP Publishing.
Nobuki Kudo and Katsuyuki Yamamoto, "Sonoporation with Microbubbles Exposed to Pulsed Ultrasound", Japanese Society for Medical and Biological Engineering, vol. 43, No. 2, pp. 231-237 (2005).
Daniel Palanker et al., "Anterior capsulotomy with a pulsed-electron avalanche knife", Journal of Cataract & Refractive Surgery, vol. 36, pp. 127-132 (Jan. 2010).
Osamu Sakai et al., "Underwater microdischarge in arranged microbubbles produced by electrolysis in electrolyte solution using fabric-type electrode", Applied Physics Letters, vol. 93, No. 23. pp. 231501-1-231501-3 (2008).
Atsushi Sugimura et al., "Denki-senkohou", Kagaku to Seibutsu, vol. 29, No. 1, pp. 54-60 (1991).
M. Kanemaru et al., "Single bubble generated by a pulsed discharge in liquids as a plasma microreactor", Plasma Sources Science and Technology, vol. 20, Article ID. 034007, pp. 1-7 (2011).
Masafumi Kashii et al., "Femtosecond Laser Processing of Protein Crystals in Crystallization Drop", Japanese Journal of Applied Physics, vol. 44, No. 27, pp. L873-L875 (2005).
Hiroki Kuriki et al., "Micro-/nanobubble-assisted Local Ablation of a Single Cell", The Robotics and Mechatronics Conference 2012 Koen Ronbunshu, The Japan Society of Mechanical Engineers, pp. 1A2-V05(1)-1A2-V05(4), (May 2012).
European Patent Office, "Extended European Search Report," issued in European Patent Application No. 13 754 261.9, which is a European counterpart of U.S. Appl. No. 14/382,012, dated Oct. 19, 2015, 9 pages.
International Search Report received for PCT Patent Application No. PCT/JP2014/072387 dated Nov. 25, 2014, 4 pages (2 pages of English Translation and 2 pages of International Search Report).
Written Opinion received for PCT Patent Application No. PCT/JP2014/072387 dated Nov. 25, 2014, 11 pages (6 pages of English Translation and 5 pages of original Written Opinion).

* cited by examiner

METHOD FOR CRYSTALLIZING PROTEIN

CROSS REFERENCE TO RELATED APPLICATIONS

This patent application is a U.S. national stage application under 35 U.S.C. § 371 of International Patent Application No. PCT/JP2014/072387 filed on Aug. 27, 2014, which claims the benefit of foreign priority to Japanese Patent Application No. JP 2013-179848 filed on Aug. 30, 2013. The International Application was published in Japanese on Mar. 5, 2015, as International Publication No. WO 2015/030038 A1 under PCT Article 21(2).

BACKGROUND OF THE INVENTION

1. Field of the Invention

The present invention relates to a bubble-jetting member and protein-adsorbing-bubble-jetting member for a protein crystal device, a protein crystal device and method for crystallizing protein, and a protein crystal-cutting device and method for cutting protein crystal, and particularly relates to a bubble-jetting member and protein-adsorbing-bubble-jetting member for a protein crystal device that are capable of jetting bubbles from a bubble-jetting port in the bubble-jetting member or jetting bubbles in which protein has been adsorbed at a boundary from the protein-adsorbing-bubble-jetting port in the protein-adsorbing-bubble-jetting member to readily generate protein crystal, a protein crystal device including the bubble-jetting member or protein-adsorbing-bubble-jetting member, and a method for crystallizing protein crystal using the protein crystal device. The present invention furthermore relates to a protein crystal-cutting device and method for cutting protein crystal in order to cut the corners of angular protein crystal or otherwise cut and shape protein crystals for use in X-ray structural analysis or the like.

2. Description of the Related Art

A structural analysis of protein crystal is indispensable in order to discover the structure and function of protein crystal. The most common technique for analyzing the structure of protein crystal is X-ray structural analysis, but a good-quality single crystal of protein must be obtained in order to analyze the three-dimensional crystal structure of protein by X-ray structural analysis.

Vapor diffusion, precipitation, and other conventional methods are known as methods for generating crystals for X-ray structural analysis of protein. However, vapor diffusion has a problem in that several weeks are required to crystallize protein and the method is time consuming. The time required in precipitation is about one week to crystallize protein and a precipitant is used; and there is therefore a problem in that the precipitant becomes an impurity and the purity of the protein crystal is reduced.

There is a known method (see Patent Document 1) for solving the above-described problem that does not require a precipitant, the method comprising a solvent-mixing step for mixing a protein containing non-crystalline protein and a smaller amount of solvent than the amount that corresponds to the saturated solubility of the protein, a resting step for resting the protein, and a stimulation-imparting step for imparting agitation, ultrasonic waves, electromagnetic waves, or other stimulation. However, the method described in Patent Document 1 has a problem in that a step for resting the protein is required and crystallization is as time-consuming as before.

A method for crystallizing protein by stimulating a solution in which protein has been dissolved (which may hereinafter be referred to as "protein solution") is also known in which a picosecond pulse laser or a femtosecond pulse laser is emitted at a protein solution (see Patent Document 2). However, there are problems in that the device for irradiating the laser is large and costly, optical equipment for irradiating the laser onto the protein solution is required, and focusing and other operations are laborious. With the method described in Patent Document 2, it is thought that an explosive phenomenon (laser ablation) occurs due to rapid light absorption at the focal point when a pulse laser is focused, the solution near the focal point suddenly evaporates, and crystal nucleus is generated due to a concentration of the solution. However, heat rapidly increases at the focal point and the protein is liable to be modified.

The corners of the resulting protein crystals are preferably removed or the protein crystals are otherwise processed into a different shape in order to analyze the three-dimensional crystal structure of protein by X-ray structural analysis, and cutting a protein crystal with a femtosecond laser is a known technique (see Non-patent Document 1). However, cutting a protein crystal using a femtosecond laser involves local high-density energy, and the protein at the cutting face of the protein crystal is liable to be modified.

[Patent Document 1] JP (Kokai) 2004-277255
[Patent Document 2] WO 2004/018744

Non-Patent Documents

[Non-patent Document 1] Masafumi Kashii, et al., "Femtosecond Laser Processing of Protein Crystals in Crystallization Drop," Japanese Journal of Applied Physics, Vol. 44, No. 27, 2005, pp. L873-L875

SUMMARY OF THE INVENTION

The present invention was devised to solve the above-described problems, and after thoroughgoing research, it was newly found that immersing a bubble-jetting port of a bubble-jetting member in a protein solution and outputting electricity to a core of the bubble-jetting member and to a counter electrode to jet bubbles from the bubble-jetting port into the protein solution allows protein crystals to be generated without imparting a heat effect on the protein solution, the bubble-jetting member comprising: a core formed of a conductive material; a shell part formed of an insulating material, the shell part including an extended section extending from the tip of the core, and at least a portion closely adhering to the core to cover the core; and a gap having a bubble-jetting port, the gap being formed between the extended section and the tip of the core.

It was also newly found that protein crystals can be generated without imparting a heat effect to the protein solution by: fabricating a protein-adsorbing-bubble-jetting member in which is arranged an outside shell part having the same concentric axis as the center axis of the shell part, the outside shell part being formed at a position away from the shell part so that a space is left therebetween, and the outside shell part having a protein-adsorbing-bubble-jetting port; and outputting electricity to the core of the protein-adsorbing-bubble-jetting member and to a counter electrode to jet bubbles, in which protein has been adsorbed, from the protein-adsorbing-bubble-jetting port.

It was newly found that protein crystal can be cut by bringing bubbles from a bubble-jetting member into contact with protein crystals in continuous fashion. The present invention was also devised on the basis of these new findings.

In other words, an object of the present invention is to provide a bubble-jetting member and protein-adsorbing-bubble-jetting member for a protein crystal device, a protein crystal device and method for crystallizing protein, and a protein crystal-cutting device and method for cutting protein crystal.

As described below, the present invention relates to a bubble-jetting member and protein-adsorbing-bubble-jetting member for a protein crystal device, a protein crystal device and method for crystallizing protein, and a protein crystal-cutting device and method for cutting protein crystal.

(1) A bubble-jetting member used in a protein crystal device, the bubble-jetting member comprising:
 a core formed of a conductive material;
 a shell part formed of an insulating material, the shell part including an extended section extending from the tip of the core, and at least a portion closely adhering to the core to cover the core; and
 a gap having a bubble-jetting port, the gap being formed between the extended section and the tip of the core.

(2) The bubble-jetting member of (1) above, wherein the extended section of the shell part is tapered.

(3) A protein-adsorbing-bubble-jetting member used in a protein crystal device, the protein-adsorbing-bubble-jetting member comprising an outside shell part on the outside of the shell part of the bubble-jetting member according to (1) or (2) above, the outside shell part having an axis coaxial with the center axis of the shell part, the outside shell part being formed at a position away from the shell part so that a space is left therebetween, and the outside shell part having a protein-adsorbing-bubble-jetting port.

(4) The protein-adsorbing-bubble-jetting member of (3) above, wherein the portion of the outside shell part formed outside the extended section is tapered.

(5) The protein-adsorbing-bubble-jetting member of (3) or (4) above, wherein a protein solution is included in the space between the shell part and the outside shell part and/or the space formed by the outside shell part and the tip of the bubble-jetting member.

(6) A protein crystal device comprising the bubble-jetting member of (1) or (2) above, a counter electrode, and electricity output means.

(7) A protein crystal device comprising the protein-adsorbing-bubble-jetting member of any of (3) to (5) above, a counter electrode, and electricity output means.

(8) A method for crystallizing protein, comprising:
 a step for immersing at least the bubble-jetting port of the bubble-jetting member of the protein crystal device of (6) above in a protein solution and allowing the counter electrode to make contact with the protein solution; and
 a step for outputting electricity to a pair of electrodes composed of the core of the bubble-jetting member and the counter electrode, and causing bubbles to be jetted from the bubble-jetting port into the protein solution.

(9) A method for crystallizing protein, comprising:
 a step for introducing a protein solution into the space between the outside shell part and the shell part of the protein-adsorbing-bubble-jetting member of the protein crystal device of (7) above and/or the space formed by the outside shell part and the tip of the bubble-jetting member;
 a step for immersing at least the protein-adsorbing-bubble-jetting port of the protein-adsorbing-bubble-jetting member in a protein solution, buffer solution, or precipitant-containing solution, and forming a state in which the core of the protein-adsorbing-bubble-jetting member and the counter electrode can be energized; and
 a step for outputting electricity to a pair of electrodes constituted by the counter electrode and the core of the protein-adsorbing-bubble-jetting member, and jetting bubbles, in which protein and/or a protein solution has been adsorbed onto the boundary, from the protein-adsorbing-bubble-jetting port into the protein solution, buffer solution, or precipitant-containing solution.

(10) The method for crystallizing protein of (9) above, wherein the protein solution is introduced into the space by a liquid feed pump, or introduced by capillary action through immersion of the protein-adsorbing-bubble-jetting port into the protein solution.

(11) A protein crystal-cutting device comprising:
 a bubble-jetting member having: a core formed of a conductive material; a shell part formed of an insulating material, the shell part including an extended section extending from the tip of the core, and at least a portion closely adhering to the core to cover the core; and a gap having a bubble-jetting port, the gap being formed between the extended section and the tip of the core;
 a counter electrode; and
 electricity output means.

(12) The protein crystal-cutting device of (11) above, wherein the extended section of the shell part is tapered.

(13) A protein crystal-cutting device comprising:
 a member for jetting bubbles in which a solution has been adsorbed onto a boundary, the member having an outside shell part, which has the same concentric axis as the center axis of the shell part, on the outside of the shell part of the bubble-jetting member of (11) or (12) above, which is formed at a position away from the shell part so that a space is left therebetween, and which has a jetting port for jetting bubbles in which a solution has been adsorbed onto the boundary;
 a counter electrode; and
 electricity output means.

(14) The protein crystal-cutting device of (13) above, wherein the portion of the outside shell part formed on the outside of the extended section is tapered.

(15) A method for cutting protein crystal, comprising:
 a step for immersing at least the bubble-jetting port of the bubble-jetting member of the protein crystal device of (11) or (12) above in a solution containing protein crystals, arranging the bubble-jetting port so that the jetted bubbles are in a position in contact with the cutting face of the protein crystals, and ensuring that the counter electrode can touch the solution containing the protein crystals; and
 a step for outputting electricity to a pair of electrodes composed of the core of the bubble-jetting member and the counter electrode, and bringing the bubbles jetted from the bubble-jetting port into contact with the cutting face of the protein crystals.

(16) A method for cutting protein crystal, comprising:
 a step for introducing a solution that can conduct electricity into a space formed between the outside shell part and the shell part and/or a space formed by the outside shell part and the tip of the bubble-jetting member, of the member for jetting bubbles in which the solution has been adsorbed onto the boundary, in the protein crystal-cutting device of (13) or (14) above;
 a step for immersing the jetting port for jetting bubbles in which the solution has been adsorbed onto the boundary in a solution containing protein crystals, arranging the jetting port so that the bubbles in which the solution has been adsorbed onto the boundary are in a position in contact with the cutting face of the protein crystals, and ensuring that the counter electrode can touch the solution containing the protein crystals; and a step for outputting electricity to a pair of electrodes composed of the counter electrode and the core of the bubble-jetting member, and allowing the bubbles jetted from the jetting port and in which the solution has been adsorbed onto the boundary to touch the cutting face of the protein crystals.

In the present invention, bubbles are jetted from a bubble-jetting port in the bubble-jetting member of a protein crystal device, and alternatively bubbles in which protein has been adsorbed at a boundary are jetted from the protein-adsorbing-bubble-jetting port in the protein-adsorbing-bubble-jetting member, whereby protein crystal can be generated. Therefore, the device can be made smaller and protein crystals can be generated with a simple operation.

Protein crystals are generated using bubbles and the protein is not liable to be modified by heat.

The protein crystal device of the present invention can be fabricated by attaching the bubble-jetting member or protein-adsorbing-bubble-jetting member to a general-purpose medical electric scalpel. Therefore, a protein crystal device can be fabricated in a simple manner and provided at low cost by combination with an existing device.

The protein crystal device and method for cutting protein crystal of the present invention cuts protein crystal using bubbles and can therefore shape protein crystal for X-ray structural analysis without the protein undergoing modification by heat.

The protein crystal device of the present invention can furthermore be used as a protein crystal-cutting device, and can therefore generate protein crystal and shape protein crystal for X-ray structural analysis using a single device.

BRIEF DESCRIPTION OF THE DRAWINGS

FIG. 6(1) is a photograph used in lieu of a drawing and is a photograph showing a lysozyme crystal in the protein solution generated in example 4, and FIG. 6(2) is a photograph used in lieu of a drawing and is a photograph showing the protein solution of comparative example 1;

FIG. 7(1) is a photograph used in lieu of a drawing and is a photograph showing a cytochrome C crystal in the protein solution generated in example 5, FIG. 7(2) is a photograph used in lieu of a drawing and is the photograph of FIG. 7(1) further enlarged, and FIG. 7(3) is a photograph used in lieu of a drawing and is a photograph showing the protein solution of comparative example 2;

FIG. 8(1) is a photograph used in lieu of a drawing and is a photograph showing a lysozyme crystal in the protein solution generated in example 7, FIG. 8(2) is a photograph used in lieu of a drawing and is a photograph showing the lysozyme crystals in the protein solution generated in example 8, and FIG. 8(3) is a photograph used in lieu of a drawing and is a photograph showing the protein solution of comparative example 3;

FIG. 9(1) is a photograph used in lieu of a drawing and is a photograph obtained prior to the bubbles making contact with the lysozyme crystals in the solution in example 9, and FIG. 9(2) is a photograph used in lieu of a drawing and is a photograph obtained after the bubbles made contact with the lysozyme crystals; and FIG. 10(1) is a photograph used in lieu of a drawing and is a photograph showing an NADH-GOGAT crystal in the protein solution generated in example 10, FIG. 10(2) is a photograph used in lieu of a drawing and is a photograph showing an NADH-GOGAT crystals in the protein solution generated in example 11, and FIG. 10(3) is a photograph used in lieu of a drawing and is a photograph showing an NADH-GOGAT crystals in the protein solution generated in example 12.

DESCRIPTION OF THE PREFERRED EMBODIMENTS

The bubble-jetting member and protein-adsorbing-bubble-jetting member for a protein crystal device, a protein crystal device and method for crystallizing protein, and a protein crystal-cutting device and method for cutting protein crystal of the present invention will be described in detail with reference to the drawings. The same reference numerals indicate the same objects in each drawing.

Figure 1:
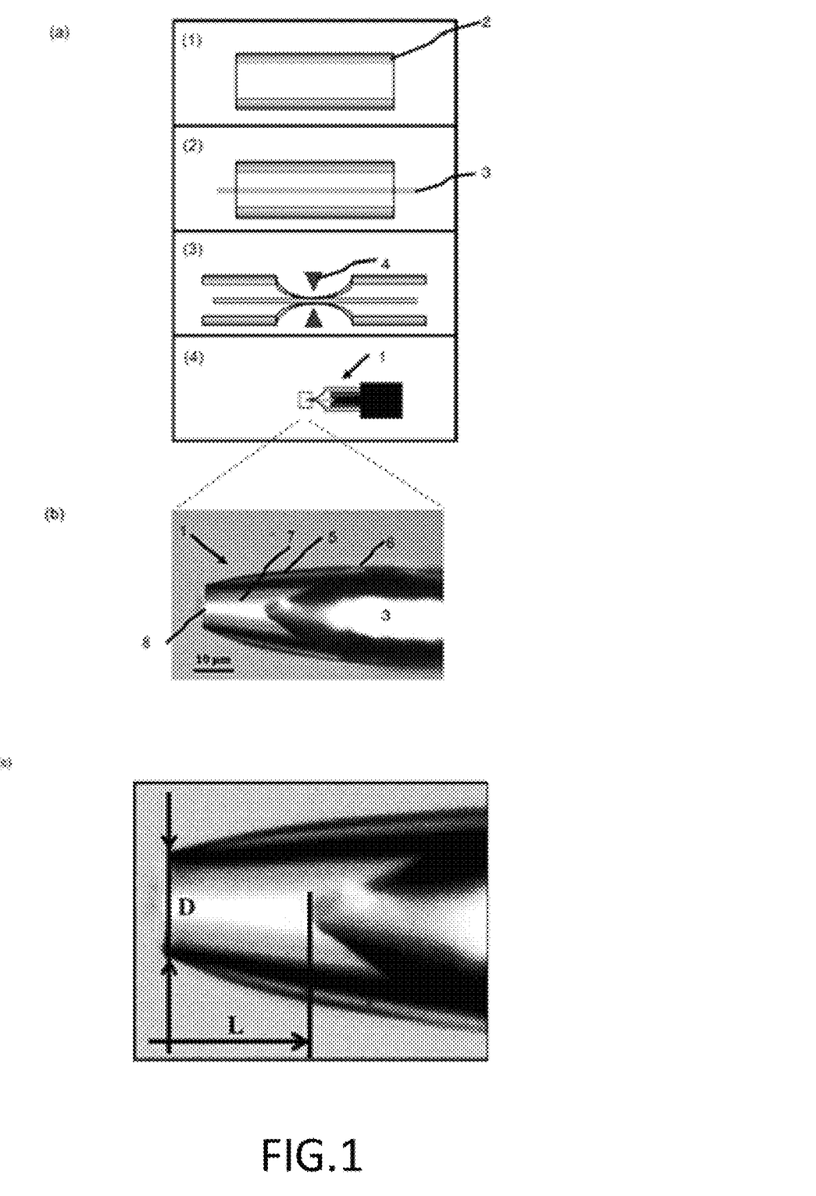
FIG. 1(a) is a drawing showing the method for producing the bubble-jetting member used in the protein crystal device of the present invention.
FIG. 1(b) is a photograph used in lieu of a drawing and is an enlarged photograph of the bubble-jetting member fabricated in example 1.
FIG. 1(c) is a photograph used in lieu of a drawing and is the photograph in FIG. 1(b) further enlarged.

FIG. 1(a) is a drawing showing an example of the method for fabricating the bubble-jetting member 1 of the present invention. In the fabrication method shown in FIG. 1(a), (1) a hollow insulating material 2 is prepared, (2) a core 3 formed of a conductive material is inserted into the hollow insulating material 2, and (3) heat 4 is applied and the insulating material is pulled apart, (4) whereupon the bubble-jetting member 1 can be fabricated. In the present production method, due to the difference in viscoelasticity between the insulating material 2 and the core 3, a shell part 6 comprising an extended section 5 in which the insulating material 2 is further extended from the tip of the core 3 is formed so as to be in close contact with the external periphery of the core 3, as shown in FIG. 1(b), and it is possible to form a bubble-jetting member 1 comprising a gap 7 formed by the extended section 5 and the tip of the core 3 and having a bubble-jetting port 8. The core 3 is endowed with a pointed shape when the bubble-jetting member 1 is fabricated using the above-described method. This is preferred in that the extended section 5 of the shell part becomes tapered and the jetted bubbles are given directionality.

There are no particular limitations as to the insulating material 2 provided it is one that insulates electricity; for example, there can be cited glass, mica, quartz, silicon nitride, silicon oxide, ceramics, alumina, and other such inorganic insulating materials, silicone rubber, ethylene propylene rubber, and other such rubber materials, ethylene vinyl acetate copolymer resins, silane-modified olefin resins, epoxy resins, polyester resins, vinyl chloride resins, acrylic resins, melamine resins, phenolic resins, polyurethane resins, polystyrene resins, fluororesins, silicone resins, polysulfide resins, polyamide resins, polyimide resins, polyethylene, polypropylene, cellulose resins, UV-curing resins, and other such insulating resins.

The conductive material forming the core 3 is not particularly limited, provided that the material can be used as an electrode. A metal is preferred, examples of which include gold, silver, copper, aluminum, and the like, as well as alloys to which small amounts of tin, magnesium, chromium, nickel, zirconium, iron, silicon, or the like, have been added. As described above, the gap 7 is formed by the tip of the core 3 and the extended section 5 in which the insulating material 2 is extended further out from the tip of the core, and therefore any combination of suitable materials such that the viscoelasticity of the insulating material 2 is greater than the viscoelasticity of the core 3 is acceptable. Examples of a combination of the insulating material 2 and the core 3 include glass and copper, glass and platinum, glass and aluminum, glass and gold, glass and silver, glass and nickel, epoxy resin and copper, epoxy resin and platinum, epoxy resin and aluminum, epoxy resin and gold, epoxy resin and silver, epoxy resin and nickel, acrylic resin and copper, acrylic resin and platinum, acrylic resin and aluminum, acrylic resin and gold, acrylic resin and silver, acrylic resin and nickel, silicone resin and copper, silicone resin and platinum, silicone resin and aluminum, silicone resin and gold, silicone resin and silver, and silicone resin and nickel.

When bubbles are to be jetted using the bubble-jetting member 1, electricity is outputted, whereupon bubbles are jetted from the bubble-jetting port 8 as though to be pulled apart once formed in the gap 7, as later described. Accordingly, there is no need to feed gas from the exterior to the bubble-jetting member 1. Consequently, the core 3 of the present invention is formed in a solid state in which the conductive material has been extended, and a tube or the like for feeding air to the interior of the core 3 is not formed, as shown in FIG. 1(b). At least a portion of the shell part 6 is configured so as to closely adhere to the core 3 near the tip of the bubble-jetting member 1 due to the difference in viscoelasticity between the insulating material 2 and core 3.

FIG. 1(c) is a further enlarged photograph of FIG. 1(b). Bubbles are continuously jetted from the bubble-jetting port 8 when electricity is outputted to the bubble-jetting member 1 of the present invention and the counter electrode 11 (not shown), and during this time, bubbles having a size approximate to the inside diameter (which may hereinafter be notated as "diameter D" or "D") of the bubble-jetting port 8 are generated in the gap 7, and the bubbles are jetted from the bubble-jetting port 8 as though to be pulled apart. Consequently, the depth of the gap 7 (the length from the tip of the core 3 to the bubble-jetting port 8; which may hereinafter be notated as "L") must at least be of a size that allows bubbles to be generated inside the gap 7, L/D preferably being at least 1. Meanwhile, the upper limit of L/D is not particularly limited as long as it is of a magnitude that allows bubbles to be continuously jetted. Since the tip of the bubble-jetting member is very narrow and readily damaged, and when consideration is given to convenience in handling, L/D is preferably 1 to 4, more preferably 1 to 3, and even more preferably 1 to 2, 1 to 2 being particularly preferred. L/D can be adjusted by varying the pull-apart speed and the temperature when heat is applied with consideration given to the relationship between the temperature and viscosity of the conductive material and the insulating material used in production.

The size of the bubbles to be jetted can be adjusted by varying the diameter D of the bubble-jetting port 8. The diameter D of the bubble-jetting port 8 is not particularly limited as long as protein crystals can be obtained by jetting bubbles into the protein solution. 1 to 50 μm is preferred, and 5 to 15 μm is more preferred. When the diameter is less than 1 μm, the possibility of generating protein crystal nuclei is reduced, and when the diameter is greater than 50 μm, considerable disturbance is imparted to the protein solution, which is undesirable in that needle crystals and/or polycrystals are liable to be generated rather than single crystals. The diameter D of the bubble-jetting port 8 can be adjusted by varying the pulling-apart speed and the temperature during heating. For the size of the bubble-jetting port 8 to be within the above-stated range, the diameter of the core 3 after pulling-apart should be 1 to 100 μm, and the insulating material 2 should be formed so as to cover the periphery of the core 3, though this may depend on the pulling-apart speed and the temperature during heating. In relation to the size of the insulating material 2 and the core 3 used for producing the bubble-jetting member 1, a material should be used which results in a diameter of 1 to 1000 μm for the core 3, and an outside diameter of 1 to 50 mm and an inside diameter of 0.5 to 40 mm for the insulating material 2, though this may depend on the pulling-apart speed and the temperature during heating.

The bubble-jetting member production method is not limited to the aforedescribed example, and production by, for example, providing the tip of the core 3 with a member of a photoresist, thermosetting resin, or the like, then providing about the circumference of the core 3 an insulating material such as silicon nitride, silicon oxide, or the like by a sputtering process, and thereafter removing the photoresist, thermosetting resin, or the like, would also be acceptable. Alternatively, the tip of the core 3 may be provided with a photoresist, thermosetting resin, or the like of tapered shape, to impart a tapered shape to the shell part subsequent to sputtering. In the case of producing the bubble-jetting member by a sputtering process, appropriate adjustments may be made to the length of the extended section 5 provided to the tip of the core 3, to adjust the aforementioned L/D.

Figure 2:
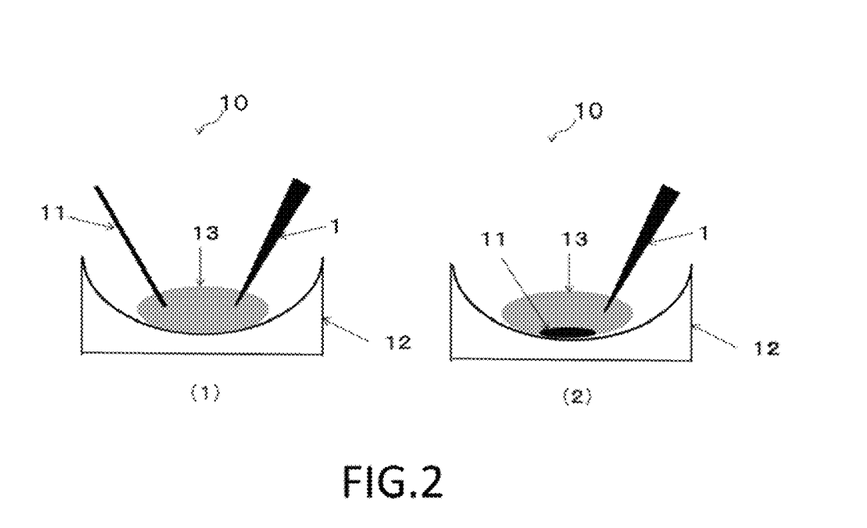
FIG. 2 is a descriptive view of the method for crystallizing protein using the protein crystal device 10 comprising the bubble-jetting member 1 of the present invention, FIG. 2(1) is an example in which the container 12 and the counter electrode 11 are separately provided, and FIG. 2(2) shows an example in which the counter electrode 11 has been affixed to the container 12.

FIG. 2 is a descriptive view of the method for crystallizing protein using the protein crystal device 10 comprising the bubble-jetting member 1 of the present invention. FIG. 2(1) shows an example of the protein crystal device 10, and includes the bubble-jetting member 1, the counter electrode 11, and electricity output means (not shown) for outputting electricity to the counter electrode 11 and the core 3, which is formed using the conductive material of the bubble-jetting member 1. When protein crystals are to be generated from the protein solution using the protein crystal device 10 shown in FIG. 2(1), a protein solution 13 is injected into a well plate or other container 12 commonly used in the field of biochemistry, at least the bubble-jetting port 8 of the bubble-jetting member 1 is immersed in the protein solution 13, the counter electrode 11 is arranged so as to be in contact with the protein solution 13, and electricity is outputted to the core 3 and the counter electrode 11.

In the present invention, the boundary of bubbles jetted from the bubble-jetting port 8 is charged. It is therefore thought that the charged protein and/or protein solution is adsorbed onto the boundary of the bubbles jetted into the protein solution 13, the protein and/or protein solution ("protein and/or protein solution" may hereinafter be described as simply as "protein") adsorbed onto the boundary of the bubbles is concentrated when the bubbles contract, and the protein is crystallized. Carboxyl and amino groups in the protein vary depending on hydrogen-ion concentration. Consequently, varying the pH allows the protein charge (plus or minus charge) to be adjusted. Therefore, the pH of the protein solution can be suitably adjusted in accordance with the type of protein and can be adjusted so as to make adsorption to the bubbles possible.

FIG. 2(2) shows another example of the protein crystal device 10, and includes the bubble-jetting member 1, a well plate or other container 12 to which the counter electrode 11 is affixed, and electricity output means (not shown) for outputting electricity to the counter electrode 11 and the core 3. An electrical circuit for connecting the counter electrode 11 and the electricity output means may be provided to the container 12, and the counter electrode 11 and the electricity output means may be connected by an electric wire or the like during use. When protein crystals are to be generated from the protein solution using the protein crystal device 10 shown in FIG. 2(2), the protein solution 13 is injected into the container 12, at least the bubble-jetting port 8 of the bubble-jetting member 1 is immersed in the protein solution 13, and electricity is outputted to the core 3 and the counter electrode 11.

The counter electrode 11 is not particularly limited as long as electricity can be conducted therethrough, it being possible to fabricate the counter electrode 11 using the same conductive material as the core 3. In the case of the example shown in FIG. 2(2), the fabricated counter electrode 11 may be welded, bonded, or otherwise provided to the container 12, and may also be sputtered or otherwise deposited onto the container. When an electric circuit is to be provided, the electric circuit may be affixed to the container, or may be sputtered or otherwise deposited on the surface of the container 12 at the same time as the counter electrode 11. In the case of either protein crystal device of FIG. 2(1) or FIG. 2(2), the counter electrode 11 should be in contact with the protein solution when the protein solution 13 is added to the container. A single well is provided to the container 12 shown in FIG. 2, but a plurality of wells may be provided to a single container 12.

Figure 3:
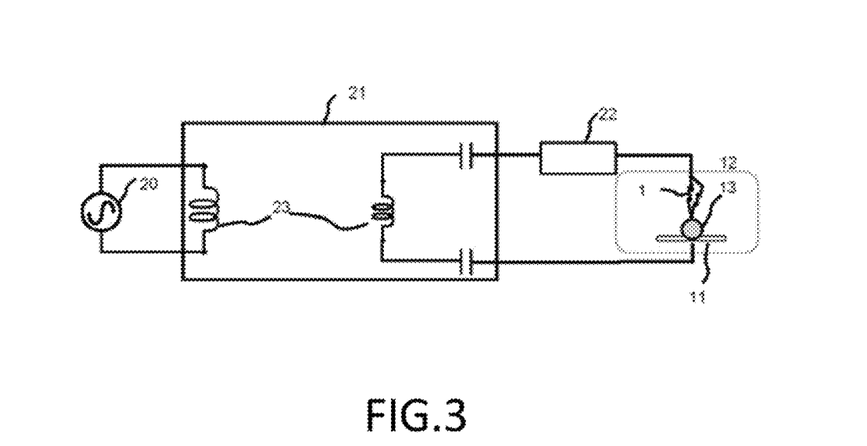
FIG. 3 is a drawing showing the overall configuration of the protein crystal device 10.

FIG. 3 is a drawing showing the overall configuration of the protein crystal device 10. The electricity output means comprises at least an ordinary commercial AC power supply unit 20, and an electric wire 21 for forming a circuit with the counter electrode 11 and the core 3 (active electrode) of the bubble-jetting member 1, and may be provided with a non-inductive resistance 22, a voltage amplification circuit 23, and a digital input/output (DIO) port or the like (not shown) as required. The electricity output means may incorporate the non-inductive resistance 22 and/or the DIO port or the like in an electric circuit for a conventional medical electric scalpel, and can be formed in a simple manner by being set in an output configuration for very small applications.

The electric current, voltage, and frequency of the electricity to be outputted to the core 3 and counter electrode 11 are not particularly limited as long as it is in a range that allows protein crystals to be generated and does not damage the bubble-jetting member 1. For example, the electric current is preferably 10 to 80 mA, and more preferably 25 to 75 mA. Bubbles may not be adequately generated when the electric current is less than 10 mA, and the electrode becomes worn when the electric current is greater than 80 mA, both of which cases being undesirable. The voltage is preferably 100 to 800 V, and more preferably 200 to 600 V. When the voltage is less than 100 V, it is difficult to generate bubbles, and when the voltage is greater than 800 V, the core 3 is liable to become worn and the bubble-jetting member 1 to become damaged, such being undesirable. The frequency is preferably 1 kHz to 1 GHz, more preferably 5 kHz to 1 MHz, and particularly preferred is 10 to 60 kHz. When the frequency is less than 1 kHz, the protein solution is subjected to appreciable shock and the bubble-jetting member 1 is liable to be damaged, and when the frequency is greater than 1 GHz, bubbles are unlikely to be generated, neither of which cases is desirable.

The solution for dissolving the protein is not particularly limited as long as electricity can be conducted therethrough and the protein does not become modified, it being possible to use a solution obtained by dissolving sodium acetate in water, or another known solution for dissolving protein. A precipitant for accelerating precipitation of the protein dissolved in the solution may be added as required within a range that does not affect the generation of crystals. The precipitant may be a water-soluble polymer, a crystallization agent, a buffer solution, or other known precipitant. Examples of the water-soluble polymer include PEG and glycerol. Examples of the crystallizing agent include sodium chloride or other metal salt, and ammonium sulfate or other ammonium salt. Examples of the buffer solution include acetic acid, phosphoric acid, and Tris. These precipitants may be used alone or in combination. The concentration of the dissolved protein may be a per-saturated state or an unsaturated state, and may be suitably adjusted as required. As described above, in the present invention, it is thought that protein is adsorbed onto the boundary of the bubbles, the protein adsorbed onto the boundary of the bubbles becomes concentrated when the bubbles contract, and the protein crystallizes. Therefore, adjusting the charge so that a considerable amount of protein adsorbs onto the boundary of the bubbles facilitates generation of protein crystals. Consequently, the protein solution is preferably supersaturated, though this is not an essential condition; the protein solution may be in an unsaturated state.

Jetting bubbles into the protein solution 13 using the protein crystal device 10 of the present invention allows protein crystals to be generated, and it is possible to grow the crystals by placing the container 12 including the generated crystals in a protein crystal growth device containing a reservoir solution having greater concentration than the protein solution in order to grow the generated crystals. The protein crystal growth device containing a reservoir solution may be a hanging-drop device, a sitting-drop device, or other known protein crystal growth device.

Figure 4:
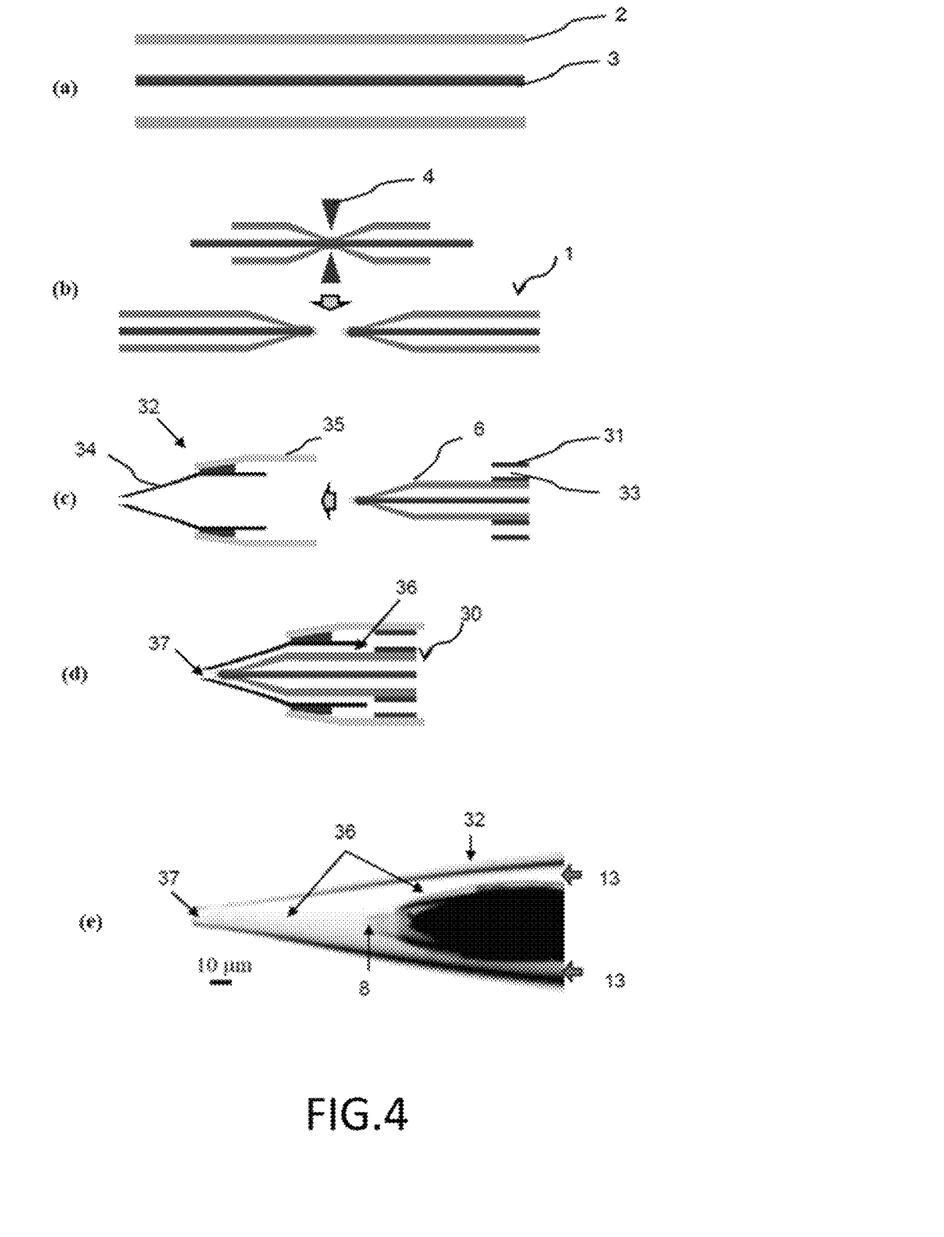
FIGS. 4(a) to 4(d) are drawings showing the method for producing the protein-adsorbing-bubble-jetting member used in the protein crystal device of the present invention.
FIG. 4(e) is a photograph used in lieu of a drawing and is an enlarged photograph of the protein-adsorbing-bubble-jetting member fabricated in example 2.

FIGS. 4(*a*) to 4(*d*) are drawings showing an outline of the procedure for fabricating a protein-adsorbing-bubble-jetting member 30 for the protein crystal device of the present invention. In the present invention, the term "protein-adsorbing bubbles" refers to bubbles to which protein and/or protein solution has been adsorbed onto the boundary. The protein-adsorbing-bubble-jetting member 30 of the present invention can be fabricated by producing the bubble-jetting member 1 using the same procedure as (1) to (4) in FIG. 1(*a*) (corresponding to (a) to (b) of FIG. 4), then fitting a coaxial positioning washer 31 fabricated by soft lithography/3D optical shaping or the like using a polymer film, rubber washer, or polydimethyl siloxane (PDMS) onto the bubble-jetting member 1, and fitting an outside shell part 32 onto the coaxial positioning washer 31, the outside shell part having an axis concentric to the center axis of the shell part 6, having a diameter greater than that of the shell part 6, and being fabricated by pulling apart a glass tube, plastic tube, or the like using heat, whereby the protein-adsorbing-bubble-jetting member 30 is fabricated having a space 36 between the outside shell part 32 and the shell part 6 of FIG. 4(d) and into which the protein solution 13 can be inserted. The washer 31 preferably includes a hole 33 to allow a pump (not shown) to feed the protein solution 13. The outside shell part 32 may be fabricated by pulling apart a glass tube or plastic tube as described above, and fitted directly onto the washer 31; or, as shown in 4(c), the outside shell part may be fabricated by adhesive bonding of a guide 35 fabricated from plastic or the like (e.g., an Eppendorf tube (an Ibis® pipette tip) IN12403Y) around pulled-apart glass 34 or the like, and the guide 35 portion then fitted onto the washer 31. The outside shell part 32 may be provided with multiple layers, so that protein solutions of different types can be introduced between the layers. Additionally, although not shown in the drawings, in the above-described FIG. 4(c), the counter electrode 11 may be arranged on the outside face of the shell part 6 or the inside face of the outside shell part 32. The material for forming the outside shell part 32 can be the same as that of the shell part 6.

The size of the protein-adsorbing bubbles to be jetted can be adjusted by varying the diameter D of the bubble-jetting port 8 and the inside diameter of a protein-adsorbing-bubble-jetting port 37. The diameter D of the bubble-jetting port 8 is preferably 1 to 50 µm, more preferably 5 to 15 µm, but is not particularly limited as long as protein is adsorbed onto the boundary of the bubbles by the bubbles being jetted into the protein solution introduced into the space 36. On the other hand, the inside diameter of the protein-adsorbing-bubble-jetting port 37 is preferably 1 to 800 µm, and more preferably 30 to 200 µm, 50 to 150 µm being particularly preferred. Feeding solution is difficult when the inside diameter of the protein-adsorbing-bubble-jetting port 37 is less than 1 µm. On the other hand, the protein sample is a very small amount, and about several microliters will therefore be the amount when the protein solution is added to the container 12. Accordingly, when the inside diameter of the protein-adsorbing-bubble-jetting port 37 is greater than 800 µm, a portion of the protein-adsorbing-bubble-jetting port 37 is liable to be outside of the protein solution 13 placed in a well, which is undesirable because the operation becomes laborious. The inside diameter of the protein-adsorbing-bubble-jetting port 37 can be adjusted by varying the temperature and the pulling-apart speed during heating.

In the case of a protein crystal device in which the protein-adsorbing-bubble-jetting member 30 is used, the counter electrode 11 can be provided separately from the protein-adsorbing-bubble-jetting member 30 as shown in FIG. 2, but the counter electrode 11 may also be provided to the protein-adsorbing-bubble-jetting member 30. When the counter electrode 11 is provided to the protein-adsorbing-bubble-jetting member 30, the counter electrode 11 may form a circuit with the core 3. Therefore, the space 36 formed by the shell part 6 and the outside shell part 32, or the space 36 formed by the tip of the bubble-jetting member 1 and the outside shell part 32 is not particularly limited as long as there is a location for contact with the introduced protein solution 13, as shown in FIG. 4(e).

When protein crystals are to be generated using a protein crystal device in which the protein-adsorbing-bubble-jetting member 30 shown in FIG. 4(e) is used, the tip of the protein-adsorbing-bubble-jetting member 30 is immersed in the protein solution 13 to introduce the protein solution to the space 36 by capillary action; alternatively, the protein solution 13 is introduced in advance to the space 36 by a pump or the like from the side opposite from the tip of the protein-adsorbing-bubble-jetting member 30. Next, at least the protein-adsorbing-bubble-jetting port 37 of the protein-adsorbing-bubble-jetting member 30 is immersed in the protein solution, buffer solution, or precipitant-containing solution, and when the counter electrode 11 is separately provided, it is brought into contact with the protein solution, buffer solution, or precipitant-containing solution, as shown in FIG. 2. Electricity is outputted to the counter electrode 11 and the core 3 of the protein-adsorbing-bubble-jetting member 30, whereby, first, bubbles are jetted from the bubble-jetting port 8, next, protein is adsorbed onto the boundary of the jetted bubbles, and protein-adsorbing bubbles can be jetted from the protein-adsorbing-bubble-jetting port 37. When the protein-adsorbing-bubble-jetting member 30 is used, the solution to be placed in the container 12 may be a protein solution, buffer solution, or precipitant-containing solution. When the concentration of the protein solution 13 introduced to the space 36 is high and the amount of protein is sufficient to generate crystals, the protein-adsorbing bubbles may be jetted into the protein solution, buffer solution, or precipitant-containing solution. On the other hand, when the concentration of the protein solution 13 introduced to the space 36 is low and the amount of protein adsorbed onto the bubbles is low, the protein-adsorbing bubbles can be jetted into the protein solution, and the solution to be injected into the container 12 can be suitably adjusted in accordance with the concentration of the protein solution 13 introduced to the space 36.

The protein solution 13 placed in the container 12 may include a precipitant as described above, but when the concentration of the precipitant is increased, the viscosity of the protein solution 13 increases. Accordingly, when the bubble-jetting member 1 is used, the jetted bubbles are less likely to migrate in the protein solution 13, and as a result, protein crystals may be generated with greater difficulty. On the other hand, when a protein-adsorbing-bubble-jetting member 30 is to be used, reducing the concentration of precipitant contained in the protein solution 13 to be introduced to the space 36 and jetting the protein-adsorbing bubbles in which protein has been sufficiently adsorbed onto the boundary of the bubbles into the protein solution makes it possible to reduce the concentration of precipitant and the amount of protein injected into the container 12. Therefore, a protein crystal device that uses the protein-adsorbing-bubble-jetting member 30 is preferably used when crystals are to be generated for a type of protein that requires a relatively high amount of precipitant for crystal generation.

The protein crystal device of the present invention can also be used as a protein crystal-cutting device without changing the configuration. When a protein crystal is to be cut using the protein-cutting device, electricity can be fed and protein crystals can be added to a solution in which protein is not modified, e.g., the solution for dissolving protein as described above, a buffer solution, or the like. When electricity is outputted to energize the core 3 and the counter electrode 11, bubbles can be continuously jetted at a high rate of several hundred to several thousand cells per second from the bubble-jetting port 8, and bringing the jetted bubbles into direct contact with the protein crystals allows the protein crystals to be cut. The electrical output of the protein crystal-cutting device can be the same as the electrical output of the protein crystal device including the bubble-jetting member 1. The present method makes it possible to cut the corners of protein crystals or perform other processing, which was conventionally difficult to do.

The protein crystal device in which the protein-adsorbing-bubble-jetting member is used may also be used as a protein crystal-cutting device. In such a case, in lieu of the protein solution, it is possible to introduce a buffer solution or other solution that can conduct electricity into the space of the protein-adsorbing-bubble-jetting member, use the protein-adsorbing-bubble-jetting member as a member for jetting bubbles in which the solution has been adsorbed onto the boundary, and bring the jetted bubbles in which the solution has been adsorbed onto the boundary into contact with protein crystals, and then cut the protein crystals.

Examples are provided below to describe the present invention in detail. However, these examples are merely for description of the present invention and are provided for reference for specific modes. These examples are for describing specific detailed modes of the present invention, and do not limit the range of the invention disclosed in the present application, and further do not represent limitations.

EXAMPLES

Example 1

Fabrication of a Bubble-Jetting Member for a Protein Crystal Device or a Protein Crystal-Cutting Device The bubble-jetting member 1 was fabricated by inserting a copper wire having a diameter of 30 μm into a hollow glass tube (made by Drummond Corp., outside diameter 1.37 mm, inside diameter 0.93 mm), and heating and pulling the glass tube apart using a glass puller (P-1000IVF made by Sutter). FIG. 1(b) is a photograph of the tip portion of the bubble-jetting member 1 fabricated in example 1, FIG. 1(c) is the photograph in FIG. 1(b) further enlarged, and the diameter D of the bubble-jetting port 8 is about 10 μm.

Example 2

Fabrication of a Protein-Adsorbing-Bubble-Jetting Member for a Protein Crystal Device The outside shell part 32 was fabricated by heating and pulling apart a hollow glass tube (made by Drummond Corp., outside diameter 33 mm, inside diameter 1.63 mm) one size greater than the hollow glass tube used to fabricate the bubble-jetting member 1 using a glass puller (P-1000IVF made by Sutter). Next, a washer fabricated by layering polymer film was fitted onto the bubble-jetting member 1 fabricated using the same procedure as example 1, and the fabricated outside shell part 32 was inserted onto the exterior of the washer to fabricate the protein-adsorbing bubble-jetting member 30. FIG. 4(e) is a photograph of the tip portion of the protein-adsorbing-bubble-jetting member 30 fabricated in example 2, and the inside diameter of the protein-adsorbing-bubble-jetting port 37 was about 100 μm.

Fabrication of a Protein Crystal Device

Example 3

The bubble-jetting member 1 fabricated in example 1 was incorporated in lieu of the scalpel in a medical electric scalpel (Hyfrecator 2000 made by ConMed Inc.), and a non-inductive resistance and DIO port were incorporated in the electricity output means to fabricate the protein crystal device 10.

Protein (Lysozyme) Crystallization

Example 4

A protein-dissolving solution was fabricated by mixing 30 μL of a 5 M NaCl solution, 46.8 μL of 80% glycerol solution (made by Wako Pure Chemical Industries), 65.7 μL of pure water, and 7.55 μL of 1 M acetate buffer (pH 5.5). Next, 1 μL of a 70-mg/mL lysozyme solution (made by Wako Pure Chemical Industries) was mixed with 1 μL of the above-described protein-dissolving solution to fabricate 2 μL of the protein solution 13.

Figure 5:
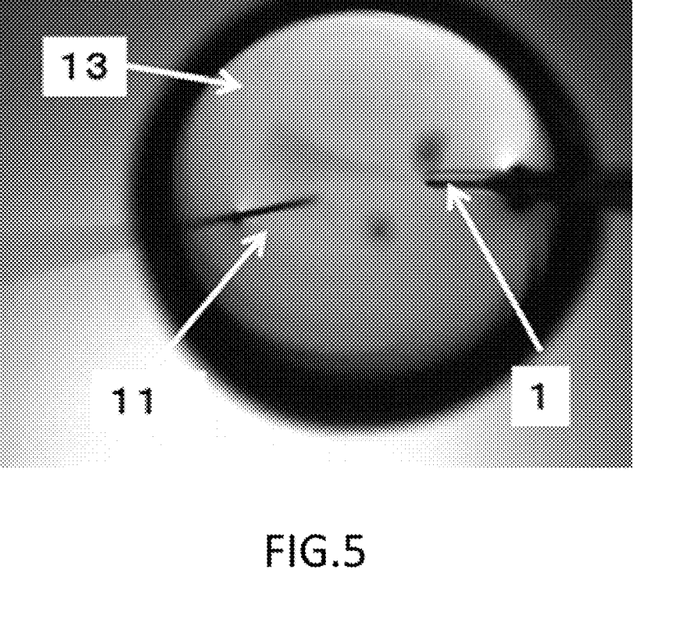
FIG. 5 is a photograph used in lieu of a drawing and is a photograph showing a state in which the counter electrode 11 and the tip portion of the bubble-jetting member 1 of the protein crystal device 10 have been inserted into the protein solution 13 in example 4.
Figure 6:
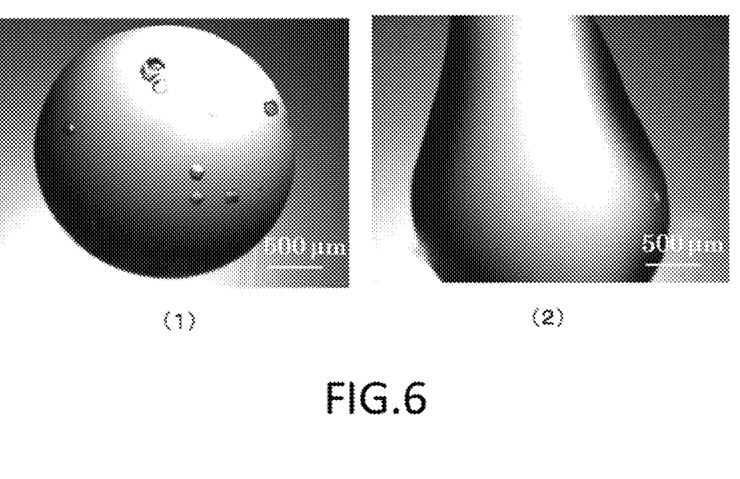
Figure 7:
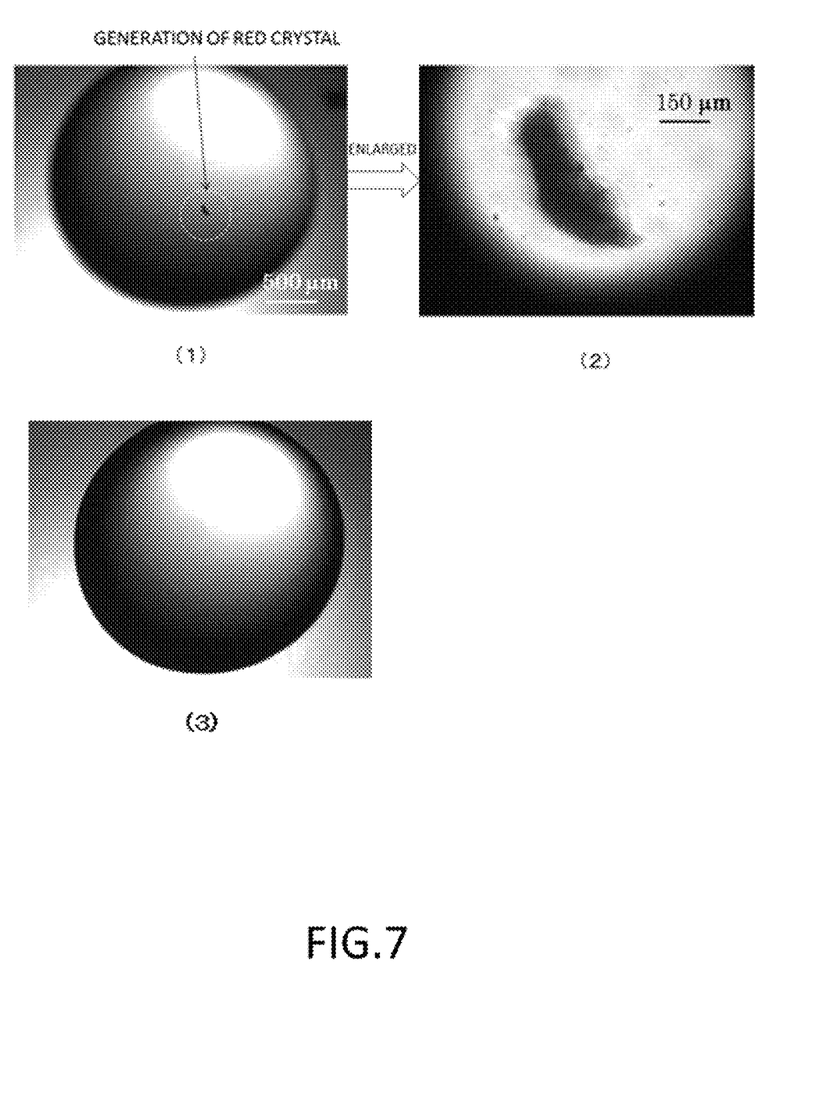
Figure 8:
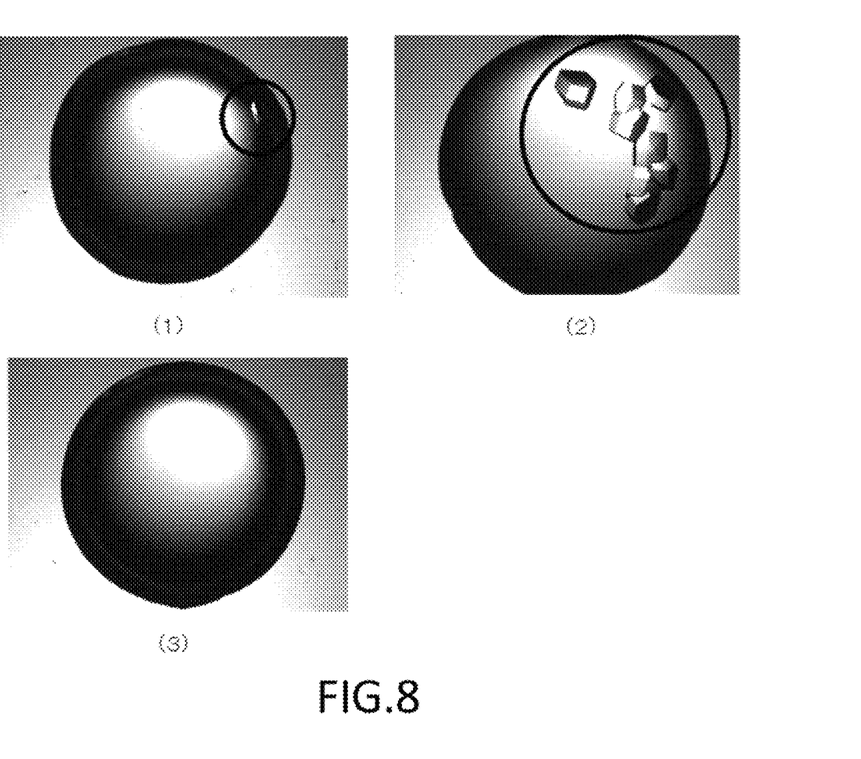
Figure 9:
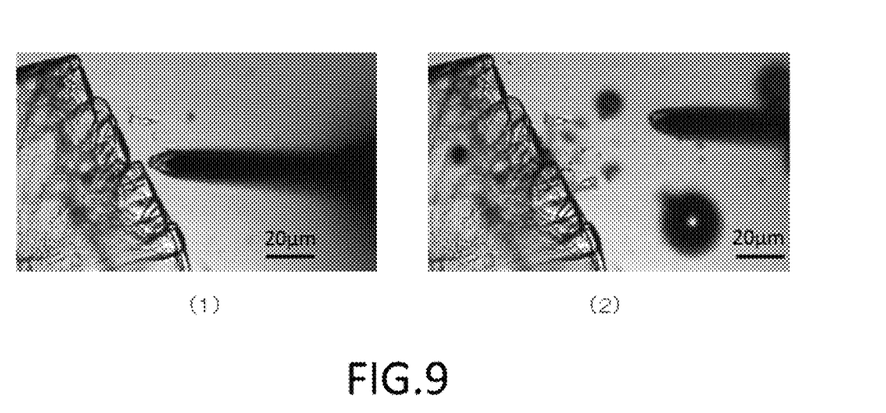
Figure 10:
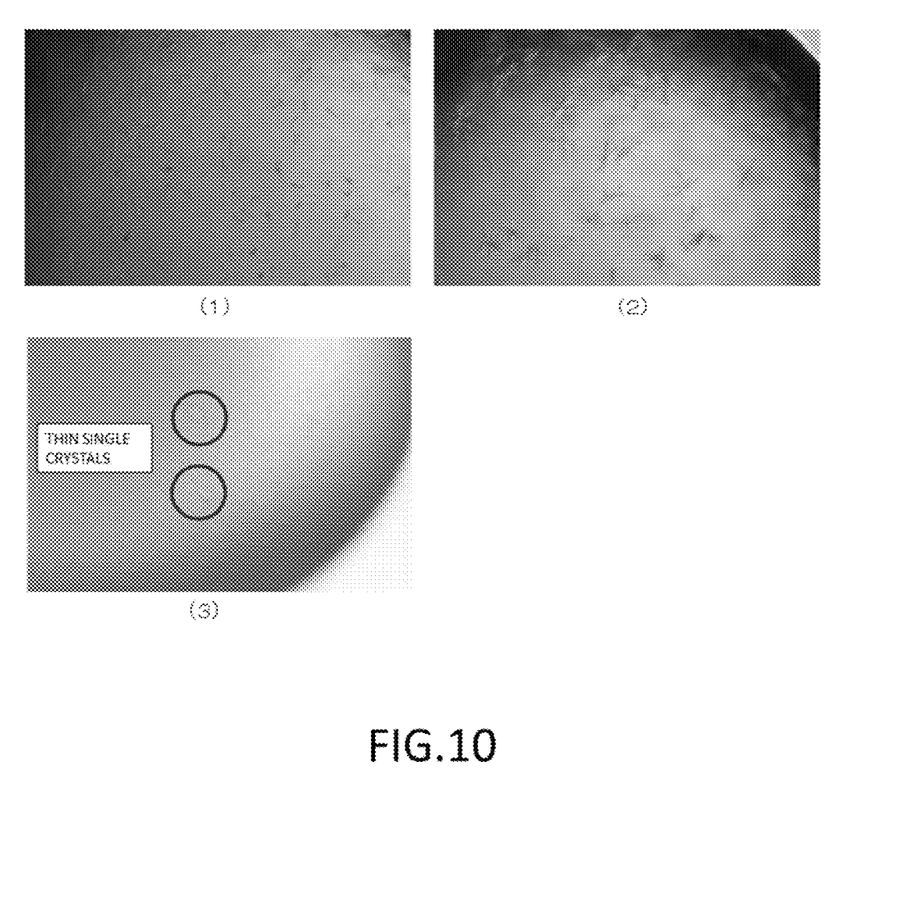

Next, the protein solution 13 was placed in a well, and a counter electrode 11 made of tungsten and the tip of the bubble-jetting member 1 of the protein crystal device 10 fabricated in example 3 were inserted into the protein solution 13 as shown in FIG. 5. Electricity was outputted to the core 3 and counter electrode 11 with a current of 27.7 mA, a voltage of 309 V, an output frequency of 32.5 kHz, a sampling frequency for impedance matching of 450 kHz, and feedback at 3.5 kHz. The electricity was outputted 10 times and bubbles were jetted into the protein solution 13. After electricity was outputted, the upper surface of the well was covered with a film, and protein crystal generation was observed. FIG. 6(1) is a photograph of the protein solution 13 after elapse of 22 hours and 50 minutes. Lysozyme crystals were confirmed to have been generated in the protein solution 13 as clearly shown in the photograph.

Comparative Example 1

Other than excluding output of electricity, generation of protein crystals was observed using the same procedure as in example 4. FIG. 6(2) is a photograph of the protein solution 13 after 22 hours and 50 minutes had elapsed. It is apparent from the photograph that generation of lysozyme crystals was not confirmed in comparative example 1.

Generating Protein (Cytochrome C) Crystals

Example 5

A protein-dissolving solution (pH 5.7) was fabricated by mixing 6 μL of a 4.0 M ammonium sulfate solution and 4 μL of a 2.5 M sodium nitrate solution. A 2 μL protein solution 13 was fabricated by mixing 1 μL of a 1-wt % cytochrome C solution (made by Sigma-Aldrich Co.) derived from bovine cardiac muscle with 1 μL of the above-noted protein-dissolving solution.

Next, protein solution 13 was placed in a well, and generation of protein crystals was observed using the same procedure as in example 4. FIG. 7(1) is a photograph of the protein solution 13 after 12 hours had elapsed, and FIG. 7(2) is an enlarged photograph of the circled portion of FIG. 7(1). It is apparent from the photograph that generation of cytochrome C crystals in the protein solution 13 was confirmed.

Comparative Example 2

Other than excluding output of electricity, generation of protein crystals was observed using the same procedure as in example 5. FIG. 7(3) is a photograph of the protein solution 13 after 12 hours had elapsed. It is apparent from the photograph that generation of cytochrome C crystals was not confirmed in comparative example 2.

Example 6

Fabrication of a Protein Crystal Device

A protein crystal device 10 was fabricated with the same configuration as that in example 3, except that the protein-adsorbing-bubble-jetting member 30 fabricated in example 2 was used in lieu of the bubble-jetting member 1 of the protein crystal device in example 3.

Generating Protein (Lysozyme) Crystals Using the Protein Crystal Device 10 Fabricated in Examples 3 and 6

Example 7

A protein-dissolving solution was fabricated by mixing 100 µL of a 5 M NaCl solution, 156.2 µL of 80% glycerol solution (made by Wako Pure Chemical Industries), 218.8 µL of pure water, and 25 µL of 1 M sodium acetate buffer (pH 4.5). Next, 1 µL of an 80-mg/mL lysozyme solution (made by Wako Pure Chemical Industries) was mixed with 1 µL of the above-described protein-dissolving solution to fabricate 2 µL of the protein solution 13.

Next, the protein solution 13 was placed in a well, and bubbles were jetted into the protein solution 13 using the same electrical output and procedure as in example 4 using the protein crystal device 10 fabricated in example 3. After electricity was outputted, the well was placed in a hanging-drop device with the protein-dissolving solution being used as a reservoir solution, and crystals were allowed to grow. FIG. 8(1) is a photograph of the protein solution 13 after 20 hours had elapsed. It is apparent from the photograph that generation of lysozyme crystals in the protein solution was confirmed.

Example 8

The growth of protein crystals was observed using the same electrical output and procedures as in example 7, except that the protein solution 13 was introduced into the space 36 using a peristaltic pump (Ring Pump RP-Q1.5S-P01A made by Aquatech) from the side opposite from the protein-adsorbing-bubble-jetting port 37 of the protein-adsorbing-bubble-jetting member 30 prior to outputting electricity using the protein crystal device 10 fabricated in example 6 in lieu of the protein crystal device 10 fabricated in example 3. FIG. 8(2) is a photograph of the protein solution 13 after 20 hours had elapsed. It is apparent from the photograph that more lysozyme crystals were generated than in example 7.

Comparative Example 3

Other than excluding output of electricity, generation of protein crystals was observed using the same procedure as in example 7. FIG. 8(3) is a photograph of the protein solution 13 after 20 hours had elapsed. It is apparent from the photograph that generation of lysozyme crystals was not confirmed in comparative example 3.

Cutting Protein Crystals

Example 9

The protein crystal device fabricated in example 3 was used as a protein crystal-cutting device and an experiment was carried out for cutting protein crystals.

First, a protein-dissolving solution was fabricated by mixing 30 µL of a 5 M NaCl solution, 46.8 µL of 80% glycerol solution (made by Wako Pure Chemical Industries), 65.7 µL of pure water, and 7.55 µL of 1 M acetate buffer (pH 4.0). Next, 1 µL of a 100-mg/mL lysozyme solution (made by Wako Pure Chemical Industries) was mixed with 1 µL of the above-described protein-dissolving solution to fabricate 2 µL of the protein solution 13. Bubbles were jetted in the protein solution 13 using the same electrical output and procedure as in example 4 and then left standing for 18 hours to prepare protein solution containing lysozyme crystals.

Next, the bubble-jetting port 8 of the bubble-jetting member 1 of the protein crystal-cutting device was arranged in a position in which the jetted bubbles were touching the cutting face of the lysozyme crystals, electricity was outputted with an electric current of 27.7 mA, a voltage of 309 V, an output frequency of 32.5 kHz, a sampling frequency of 450 kHz for impedance matching, and feedback at 3.5 kHz, and bubbles were brought into contact with the lysozyme crystals. FIG. 9(1) is a photograph obtained prior to the bubbles making contact with the lysozyme crystals, and FIG. 9(2) is a photograph obtained after the bubbles made contact with the lysozyme crystals. It is apparent from FIGS. 9(1) and (2) that protein crystals were successfully cut by bringing bubbles into contact with protein crystals.

Generating Protein (NADH-GOGAT) Crystals Using the Protein Crystal Device 10 Fabricated in Example 3

Example 10

Next, NADH-dependent glutamate synthase (NADH-GOGAT), which is a protein that is difficult to crystallize, was crystallized. Ordinarily, about 25% PEG6000 precipitant must be added to obtain NADH-GOGAT crystals, but a precipitant is an impurity and only needle crystals unsuitable for structural analysis can be obtained.

A protein-dissolving solution was fabricated by mixing pure water with NaCl to a concentration of 100 mM, 2-oxoglutaric acid (2-OG, made by Wako Pure Chemical Industries) to a concentration of 4 mM, azaserine (made by Sigma-Aldrich) to a concentration of 4 mM, Tris-HCl to a concentration of 100 mM (pH 7.5), glycerol (made by Wako Pure Chemical Industries) to a concentration of 12 v/v %, and PEG6000 (made by Hampton Research) to a concentration of 20 w/v %. Next, 1 µL of a 80-mg/mL NADH-GOGAT solution (obtained by cloning cyanobacterium *Leptolyngbya borynana* genes. The cloning procedure is found in Okuhara, H., Matsumura, T., Fujita, Y., and Hase, T., 1999, Plant Physiol. 120, 33-42.) and 1 µL of the above-described protein-dissolving solution were mixed together to fabricate 2 µL of the protein solution 13. The ultimate concentration of PEG6000 in the protein solution was 10 w/v %.

Next, the protein solution 13 was placed in a well, and bubbles were jetted in the protein solution 13 with the same electrical output and procedure as in example 4 using the protein crystal device 10 fabricated in example 3. After electricity was outputted, the well was placed in a hanging-drop device with a reservoir solution, and crystals were allowed to grow. The reservoir solution was obtained by mixing pure water with Tris-HCl to a concentration of 85 mM (pH 8.5), sodium acetate trihydrate (made by Hampton Research) to a concentration of 0.17 mM, PEG6000 (made by Hampton Research) to a concentration of 14 w/v %, and glycerol (made by Wako Pure Chemical Industries) to a concentration of 10.5 v/v %. FIG. 10(1) is a photograph of the protein solution 13 after two weeks had elapsed.

Example 11

Crystals were grown using the same procedure as in example 10, except that the concentration of PEG6000 in the protein-dissolving solution was set to 16 w/v % and the concentration of glycerol was set to 10.5 v/v % to thereby obtain an ultimate concentration of PEG6000 in the protein solution of 8 w/v %, the concentration of PEG6000 in the reservoir solution was 8 w/v %, and the glycerol concentration was 5.25 v/v %. FIG. 10(2) is a photograph of the protein solution 13 after two weeks had elapsed.

Example 12

Crystals were grown using the same procedure as in example 10, except that the concentration of PEG6000 in the protein-dissolving solution was set to 12 w/v % and the concentration of glycerol was set to 9.0 v/v % to thereby obtain an ultimate concentration of PEG6000 in the protein solution of 6 w/v %, the concentration of PEG6000 in the reservoir solution was 6 w/v %, and the glycerol concentration was 4.5 v/v %. FIG. 10(3) is a photograph of the protein solution 13 after two weeks had elapsed.

It is apparent from the photographs in FIGS. 10(1) to (3) that protein crystals were successfully obtained by jetting bubbles into a protein solution, even when the concentration of the PEG6000 precipitant in the protein solution was 10 w/v % or less. Single NADH-GOGAT crystals were obtained when the PEG concentration in the protein solution was reduced to 6 w/v %, as shown in FIG. 10(3). Using the protein crystal device of the present invention makes it not only possible to obtain crystals even with a reduced concentration of PEG6000 precipitant, but adjusting the concentration of PEG6000 also makes it possible to differentiate and fabricate needle crystals and single crystals. Furthermore, since single crystals can be fabricated, there is expectation for structural analysis of NADH-GOGAT.

INDUSTRIAL APPLICABILITY

Incorporating the bubble-jetting member and protein-adsorbing-bubble-jetting member for a protein crystal device according to the present invention into a conventional general-purpose medical electric scalpel or the like makes it possible to fabricate a protein crystal device in a simple manner. The protein crystal device of the present invention is not liable to modify protein with heat because protein crystals are generated using bubbles. The protein crystal device of the present invention can furthermore be used as a protein crystal-cutting device, and can therefore generate protein crystals and shape protein for X-ray structural analysis using a single device. Therefore, the present invention can be used in the analysis of protein crystal structure in medical facilities, universities, industry, and other research facilities.

KEY

1 Bubble-jetting member
2 Insulating material
3 Core (conductive material)
5 Extended section
6 Shell part
7 Gap
8 Bubble-jetting port
10 Protein crystal device
11 Counter electrode
12 Container
13 Protein solution
20 Ordinary commercial AC power supply unit
21 Electric wire
22 Non-inductive resistance
23 Voltage amplification circuit
30 Protein-adsorbing-bubble-jetting member
31 Coaxial positioning washer
32 Outside shell part
33 Hole
34 Glass
35 Guide
36 Space
37 Protein-adsorbing-bubble-jetting port

What is claimed is:

1. A method for crystallizing protein using a protein crystal device,
   the protein crystal device comprising:
   a bubble-jetting member, a counter electrode, and an electricity output means,
   the bubble-jetting member comprising:
   a core formed of a conductive material;
   a shell part formed of an insulating material, the shell part including an extended section extending from a tip of the core, and at least a portion closely adhering to the core to cover the core; and
   a gap having a bubble-jetting port, the gap being formed between the extended section and the tip of the core; and
   the method for crystallizing protein comprising:
   a step for immersing at least the bubble-jetting port of the bubble-jetting member of the protein crystal device in a protein solution and allowing the counter electrode to make contact with the protein solution; and
   a step for outputting electricity to a pair of electrodes composed of the core of the bubble-jetting member and the counter electrode, and causing bubbles to be jetted from the bubble-jetting port into the protein solution;
   wherein the method for crystallizing protein is done in vitro.

2. The method for crystallizing protein using the protein crystal device of claim 1, wherein the protein solution comprises a precipitant.

3. The method for crystallizing protein using the protein crystal device of claim 2, wherein the precipitant is selected from PEG and Tris.

4. A method for crystallizing protein using a protein crystal device,
   the protein crystal device comprising:
   a protein-adsorbing-bubble-jetting member, a counter electrode, and an electricity output means,
   the protein-adsorbing-bubble-jetting member comprising:
   a core formed of a conductive material;
   a shell part formed of an insulating material, the shell part including an extended section extending from a tip of the core, and at least a portion closely adhering to the core to cover the core;
   a gap having a bubble-jetting port, the gap being formed between the extended section and the tip of the core; and an outside shell part on the outside of the shell part;
wherein
   the outside shell part has an axis coaxial with the center axis of the shell part,
   the outside shell part is formed at a position away from the shell part so that a space is left therebetween, and
   the outside shell part has a protein-adsorbing-bubble-jetting port,
the method for crystallizing protein comprising:
a step for introducing a protein solution into the space between the outside shell part and the shell part of the protein-adsorbing-bubble-jetting member of the protein crystal device and/or the space formed by the outside shell part and a tip of the extended section of the shell part;

a step for immersing at least the protein-adsorbing-bubble-jetting port of the protein-adsorbing-bubble-jetting member in a protein solution, buffer solution, or precipitant-containing solution, and forming a state in which the core of the protein-adsorbing-bubble-jetting member and the counter electrode can be energized; and a step for outputting electricity to a pair of electrodes constituted by the counter electrode and the core of the protein-adsorbing-bubble-jetting member, and jetting bubbles, in which protein and/or a protein solution has been adsorbed onto the boundary, from the protein-adsorbing-bubble-jetting port into the protein solution, buffer solution, or precipitant-containing solution.

5. The method for crystallizing protein using the protein crystal device of claim 4, wherein the protein solution is introduced into the space by a liquid feed pump, or introduced by capillary action through immersion of the protein-adsorbing-bubble-jetting port into the protein solution.

* * * * *